United States Patent [19]

Alzner

[11] Patent Number: 5,116,652
[45] Date of Patent: May 26, 1992

[54] KINK-RESISTANT MEDICAL TUBING AND CATHETERS

[75] Inventor: Bernard G. Alzner, Round Lake, Ill.

[73] Assignee: Abbott Laboratories, Abbott Park, Ill.

[21] Appl. No.: 421,420

[22] Filed: Oct. 13, 1989

[51] Int. Cl.$^5$ .............................. B32B 1/08
[52] U.S. Cl. ........................ 428/36.9; 428/36.91; 604/264; 604/280; 525/123; 525/131; 525/183; 525/919
[58] Field of Search .............. 428/36.9, 36.91; 604/264, 265, 266, 280, 282; 525/123, 131, 183, DIG. 919

[56] References Cited

U.S. PATENT DOCUMENTS 4,616,064 10/1986 Zukosky et al. .................. 525/92
4,686,124 8/1987 Onohara et al. .................. 604/265

*Primary Examiner*—Ellis P. Robinson
*Assistant Examiner*—J. Weddington
*Attorney, Agent, or Firm*—A. Nicholas Trausch; Clifford A. Dean

[57] ABSTRACT

Medical tubing is extruded from a composition of a divalent metal ionomer, polyamide and polyurethane, preferably in the ranges of 60–80% of ionomer, 10≧25% polyamide and 10–20% polyurethane. After extrusion the tubing may be sterilized with ethylene oxide or gamma irradiation. The tubing is substantially kink-resistant and the degree of stiffness and mechanical strength can be adjusted by varying the amount of polyamide and polyurethane so that the tubing can efficiently function as a catheter.

8 Claims, No Drawings

KINK-RESISTANT MEDICAL TUBING AND CATHETERS

TECHNICAL FIELD

This invention relates to medical tubing and catheters and, more particularly, to tubing and catheters that are substantially resistant to kinks and fluid flow blockage.

BACKGROUND OF THE INVENTION

Medical tubing and catheters are widely employed for many treatment and diagnostic procedures involving the administration of fluid medications to the patient and the removal of fluids from the patient. In the broadest sense, medical tubing and catheters are synonymous, a catheter being merely a tube with an appropriately formed tip. However, the ultimate use for which medical tubing is designed requires that the tubing have certain physical characteristics. For example, a catheter must be sufficiently stiff or rigid to enable its insertion and movement through narrow body orifices and channels. On the other hand, tubing as well as a catheter, must be sufficiently flexible so that it may readily conform to body shapes and also be conveniently connectable to medication reservoirs or fluid evacuation containers. In addition, a catheter must be of sufficient mechanical strength to resist tear in normal use, i.e., removed against tissue resistance.

During actual use with a patient, medical tubing is often subjected to forces or stresses that affect its ability to properly function. For example, the patient may roll over onto the tubing and thereby tend to collapse, pinch or bend it. Where a substantial length of tubing is employed, the same can become snagged, knotted or sharply bent to form a kink which impedes or blocks fluid flow. Similarly, catheters placed inside the body can be subjected to twisting and kinking motions due to movement of muscles, bones, etc., adjacent to or surrounding the catheter. Pinch valves or the like also create potentially destructive compressive forces. Obviously, any blockage or impediment of fluid flow can create serious health problems. It is thus recognized by those skilled in the art that medical tubing desirably should be able to resist collapse and the formation of kinks and also be able to quickly and completely recover from the imposition of such forces.

Medical tubing and catheters are generally made by well known extrusion processes of single polymers The most widely used materials of construction are thermoplastic polyamides (nylons), Teflons and polyurethanes, which possess a wide range of stiffness and mechanical strength properties. Experience has shown that they either suffer from an inability to quickly and completely recover from severe strains applied thereto or exhibit low mechanical strength or poor kink recovery properties Flexible materials known to possess good elastic recovery are too soft for proper insertion. Rigid materials needed for their abuse resistance exhibit poor recovery from kinks No single material is known to meet all the above mentioned characteristics.

There thus exists a need for medical tubing and catheters constructed of materials so that they are substantially kink-resistant and also have sufficient mechanical strength and stiffness to perform their intended functions.

BRIEF SUMMARY OF THE INVENTION

The present invention provides medical tubing that is substantially kink-resistant and also has stiffness and mechanical strength characteristics enabling it to function as a catheter As used herein, the word "kink" in intended to apply broadly to any stress, bend or collapse that tends to restrict fluid flow through the tubing; and the phrase "kink-resistant", or the like, is intended to apply to the ability to resist such flow-restricting conditions as well as the ability to substantially completely recover from sever kink-causing stresses.

According to practice of the invention, the tubing comprises a blend of an ionomer and one or more additional polymers, within ranges that include 100% of the ionomer. Tubing of 100% ionomer is ideal for plain liquid-carrying applications, but lacks the mechanical strength required for catheter use. As the percentages of the second and/or third materials of the thermoplastic blend are increased, the mechanical strength of the tubing extruded therefrom is increased thereby making the tubing suitable for catheter applications. In all ranges of the blend of materials, the tubing of the invention is substantially kink-resistant.

Other features and advantages of the invention will be apparent from the following detailed description and claims.

DETAILED DESCRIPTION OF THE INVENTION

The present invention grows out of the need for better kink-resistant medical tubing and the discovery that extruded tubing formed of a divalent metal ionomer exhibits a remarkable ability to resist and recover from kinks. In general, an ionomer comprises a copolymer of an olefin and a carboxylic acid cross-linked through neutralization of the acid moiety with a metal cation. Commercially available ionomers, such as those sold by DuPont under the trademark Surlyn, and designations F 1801 and 9721, comprise a copolymer of ethylene and acrylic acid and, more particularly, a terpolymer of zinc acrylate.

According to DuPont's U.S. Trademark Registration No. 793,497, for Surlyn, the composition has been in use as a raw material since around 1963. Nonetheless, it would appear that Surlyn has never been considered for use as medical tubing and catheters.

Typically, medical catheters of interest are extruded and ranges in dimension from inner diameters of about 0.010–0.030 inches, outer diameters of about 0.022–0.050 inches and thicknesses of about 0.006–0.010 inches. In practicing the present invention, tubing within the ranges indicated is extruded from polymers having the composition of 50–100% Surlyn, 0–25% polyamide such as that sold by Huls America under the trade designation Vestamid E62M-53, and 0–25% polyurethane, such as that sold by Dow Chemical under the trade designation Pellethane 2363-75D. The preferred composition is a blend of 60–80% Surlyn, 10–25% polyamide and 10–20% polyurethane. An increase in the percentages of polyamide and/or polyurethane results in an added degree of mechanical strength in the tubing. Polyamide increases the mechanical strength to a greater extent than polyurethane, but significantly reduces stiffness. Polyurethane maintains the stiffness properties of the Surlyn. All tubing within the ranges given is substantially kink-resistant.

Medical tubing is conventionally sterilized by treatment of the same with ethylene oxide (EtO) or high energy gamma irradiation. In that regard, it has been discovered that sterilization of the tubing of the invention by either means results in further enhancement of the desired tubing characteristics, including improved stiffness and kink-resistance.

If desired, fillers such as radiopaquing materials and colorants may be added to the blend. However, such materials may be considered neutral and have no effect on the desired characteristics of kink-resistance, stiffness, and mechanical strength.

Preferred compositions are shown in the following examples:

| | | |
|---|---|---|
| (1) | Surlyn F 1801 | 60% |
| | Vestamid E62M-53 | 20% |
| | Pellethane 2363-75D | 20% |
| (2) | Surlyn 9721 | 80% |
| | Vestamid E62M-S3 | 10% |
| | Pellethane 2363-75D | 10% |
| (3) | Surlyn F1801 | 60% |
| | Vestamid E62M-53 | 10% |
| | Pellethane 2363-75D | 10% |
| | Barium sulfate | 20% |
| (4) | Surlyn 9721 | 85% |
| | Pellethane 2363-75D | 15% |
| (5) | Surlyn F1801 | 70% |
| | Vestamid E62M-S3 | 20% |
| | Pellethane 2363-75D | 10% |
| (6) | Same as (5), but substitute | |
| | Pellethane 2363-65D | |

The barium sulfate in Example (3) is used to provide radiopaque properties in the tubing.

After extrusion, tubing made in accordance with the foregoing examples was sterilized by treatment via EtO and, separately, gamma irradiation, whereupon it was observed that the tensile modulus and kink-resistance of the tubing was further increased.

Other co- and terpolymers of ethylene, propylene and bivalent meta acrylates are also suitable and may be substituted for the Suryn. Similarly, other suitable polyamide and polyurethane polymers which exhibit and above mentioned properties may be substituted for the Vestamid and Pellethane, respectively.

While preferred embodiments have been described, changes and variations may be made by those skilled in the art without departing from the spirit and scope of the invention as defined in the appended claims.

What is claimed:

1. Medical tubing comprising an extruded product of a composition consisting essentially of about 60 to about 80% of a terpolymer of ethylene, acrylic acid, and zinc acrylate, about 10 to about 25% of polyamide, and about 10 to about 20% of polyurethane.

2. Medical tubing according to claim 1 which is treated with ethylene oxide.

3. Medical tubing according to claim 1 which is treated with gamma irradiation.

4. Medical tubing according to claim 1 wherein said composition comprises 60% of said terpolymer, 20% polyamide and 20% polyurethane.

5. Medical tubing according to claim 1 wherein said composition comprises 80% of said terpolymer, 10% polyamide and 10% polyurethane.

6. Medical tubing according to claim 1 wherein said composition comprises 60% of said terpolymer, 10% polyamide, 10% polyurethane and 20% barium sulfate.

7. Medical tubing according to claim 1 wherein said composition comprises 85% of said terpolymer and 15% polyurethane.

8. Medical tubing according to claim 1 wherein said composition comprises 70% of said terpolymer, 20% polyamide and 10% polyurethane.

* * * * *

UNITED STATES PATENT AND TRADEMARK OFFICE
CERTIFICATE OF CORRECTION

PATENT NO. : 5,116,652
DATED : May 26, 1992
INVENTOR(S) : Bernard G. Alzner

It is certified that error appears in the above-indentified patent and that said Letters Patent is hereby corrected as shown below:

Column 1, line 49, delete "polymers" and insert --polymers --.
Column 1, line 57, delete "properties" and insert --properties --.
Column 1, line 61, delete "kinks" and insert --kinks --.
Column 2, line 6,  delete "catheter" and insert --catheter --.
Column 2, line 12, delete "sever" and insert -- severe --.
Column 4, line 4, delete " meta" and insert --metal --.
Column 4, line 5, delete Suryn" and insert --Surlyn --.
Column 4, line 6, delete "and and insert --the --.

Signed and Sealed this

Fourteenth Day of September, 1993

Attest:

BRUCE LEHMAN

*Attesting Officer*           *Commissioner of Patents and Trademarks*